(12) United States Patent
Gaudernack et al.

(10) Patent No.: US 7,375,117 B2
(45) Date of Patent: May 20, 2008

(54) POLYPEPTIDES

(75) Inventors: Gustav Gaudernack, Oslo (NO); Stein Sæøe-Larssen, Oslo (NO); Mona Møller, Porsgrunn (NO); Jon Amund Eriksen, Porsgrunn (NO)

(73) Assignee: GemVax AS, Oslo (NO)

( * ) Notice: Subject to any disclaimer, the term of this patent is extended or adjusted under 35 U.S.C. 154(b) by 0 days.

(21) Appl. No.: 11/391,497

(22) Filed: Mar. 29, 2006

(65) Prior Publication Data

US 2006/0194731 A1 Aug. 31, 2006

Related U.S. Application Data

(62) Division of application No. 10/451,050, filed as application No. PCT/NO01/00498 on Dec. 18, 2001.

(30) Foreign Application Priority Data

Dec. 22, 2000 (GB) ................................ 0031430.2

(51) Int. Cl.
*A01N 43/40* (2006.01)
(52) U.S. Cl. ...................... 514/325; 514/330
(58) Field of Classification Search ............ None
See application file for complete search history.

(56) References Cited

U.S. PATENT DOCUMENTS

| 2006/0106196 A1 | 5/2006 | Gaudernack et al. | 530/326 |
| 2007/0004632 A1 | 1/2007 | Gaudernack et al. | 514/14 |

FOREIGN PATENT DOCUMENTS

| WO | WO 99/01560 | 1/1999 |
| WO | WO 99/50386 | 10/1999 |
| WO | WO 99/50392 | 10/1999 |
| WO | WO 00/02581 | 1/2000 |
| WO | WO 00/61766 | 10/2000 |

OTHER PUBLICATIONS

Gaiger et al. (Blood, vol. 96, No. 4, Aug. 2000, pp. 1480-1489).*
Dermer (Bio/Technology, 1994, 12:320).*
Wick, M. et al., 1999, Gene 232: 97-106.*
Vonderheide, et al., "The Telomerase Catalytic Subunit is a Widely Expressed Tumor-Associated Antigen Recognized by Cytotoxic T Lymphocytes," *Immunity*, vol. 10, 1999, pp. 673-679.
Abstract No. 2999 (Vonderheide, et al., "Generation of Telomerase-Specific HLA-A3-Restricted Cytotoxic T Lymphocytes from Patient Blood: Implications for Widely Applicable Anti-cancer Immunotherapy"), *Blood*, vol. 94, 1999, p. 677a.
Abstract No. 2058 (Vonderheide, et al., "Search for Universal Tumor Antigens: Potential of the Catalytic Telomerase Subunit"), *Blood*, vol. 92, Supp. 10, 1998, p. 500a.
Wick, et al., "Genomic Organization and Promoter Characterization of the Gene Encoding the Human Telomerase Reverse Transcriptase (hTERT)," *Gene*, vol. 232, 1999, pp. 97-106.
Dong Seok Kim et al., "Saxatilin, a Snake Venom Disintegrin, Suppresses TNF-α-Induced Ovarian Cancer Cell Invasion," Journal of Biochemistry and Molecular Biology, Mar. 2007; 40(2): 290-294.
Savita Bisht et al., "Polymeric Nanoparticle-Encapsulated Curcumin ("Nanocurcumin"): A Novel Strategy for Human Cancer Therapy," Journal of Nanobiotechnology, Apr. 17, 2007; 5(3): http://www.jnanobiotechnology.com/content/5/1/3.

* cited by examiner

*Primary Examiner*—Cecilia J. Tsang
*Assistant Examiner*—Thomas S. Heard
(74) *Attorney, Agent, or Firm*—Fitzpatrick, Cella, Harper & Scinto

(57) ABSTRACT

The present invention relates to polypeptides, and nucleic acids DNA encoding these polypeptides, capable of eliciting an immune reaction against cancer, methods for generating T lymphocytes capable of recognizing and destroying tumor cells, and pharmaceutical compositions for the treatment, prophylaxis or diagnosis of cancer.

13 Claims, 9 Drawing Sheets

```
              643       653       663       673       683       693
          ...|....|....|....|....|....|....|....|....|....|....|....|
hTERT     NMDYVVGARTFRREKRAERLTSRVKALFSVLNYERARRPGLLGASVLGLDDIHRAWRTF
γ-ins     NMDYVVGARTFRREKRAERLTSRVKALFSVLNYERARRPGLLGASVLGLDDIHRAWRTF
Ins-4     NMDYVVGARTFRREKRAERLTSRVKALFSVLNYERARRPGLLGASVLGLDDIHRAWRTF
β-del     NMDYVVGARTFRREKRAERLTSRVKALFSVLNYERARRPGLLGASVLGLDDIHRAWRTF
α-del     NMDYVVGARTFRREKRAERLTSRVKALFSVLNYERARRPGLLGASVLGLDDIHRAWRTF
σ-ins     NMDYVVGARTFRREKPVAVLWFNFLFKQKPSVSPRG 703       713       723       733       743       753
          ...|....|....|....|....|....|....|....|....|....|....|....|
hTERT     LRVRAQDPPPELYFVKVDVTGAYDTIPQDRLTEVIASIIKPQNTYCVRRYAVVQKAAHG
γ-ins     LRVRAQDPPPELYFVKVDVTGAYDTIPQDRLTEVIASIIKPQNTYCVRRYAVVQKAAHG
Ins-4     LRVRAQDPPPELYFVKVDVTGAYDTIPQDRLTEVIASIIKPQNTYCVRRYAVVQKAAHG
β-del     LRVRAQDPPPELYFVKVDVTGAYDTIPQDRLTEVIASIIKPQNTYCVRRYAVVQKAAHG
α-del     LRVRAQDPPPELYFVK~~~~~~~~~~~~~DRLTEVIASIIKPQNTYCVRRYAVVQKAAHG 763       773       783       793       803       813
          ...|....|....|....|....|....|....|....|....|....|....|....|
hTERT     VRKAFKSHVSTLTDLQPYMRQFVAHLQETSPLRDAVVIEQSSSLNEASSGLFDVFLRFM
γ-ins     VRKAFKSHVSTLTDLQPYMRQFVAHLQETSPLRDAVVIEQSSSLNEASSGLFDVFLRFM
Ins-4     VRKAFKSHVSTLTDLQPYMRQFVAHLQETSPLRDAVVIEQSSSLNEASSGLFDVFLRFM
β-del     VRKAFKSHVLRPVPGEPAGLPPHAALQPVLRRTEQAVCGDSAGRAAPAEGG 823       833       843       853       863       873
          ...|....|....|....|....|....|....|....|....|....|....|....|
hTERT     HHAVRIRGKSYVQCQGIPQGSILSTLLCSLCYGDMENKLFAGIRRDGLLLRLVDDFLLV
γ-ins     HHAVRIRGKSYVQCQGIPQGSILSTLLCSLCYGDMENKLFAGIRRDGLLLRLVDDFLLV
Ins-4     HHAVRIRGKSYVQCQGIPQGSILSTLLCSLCYGDMENKLFAGIRRDGLLLRLVDDFLLV 883       893       903       913       923       933
          ...|....|....|....|....|....|....|....|....|....|....|....|
hTERT     PHLTHAKTFLRTLVRGVPEYGCVVNLRKTVVNFPVEDEALGGTAFVQMPAHGLFPWCGL
γ-ins     PHLTHAKTFLRTLVRGVPEYGCVVNLRKTVVNFPVEDEALGGTAFVQMPAHGLFPWCGL
Ins-4     PHLTHAKTFLRTLVRGVPEYGCVVNLRKTVVNFPVEDEALGGTAFVQMPAHGLFPWCGL 943       953       963       973       983       993
          ...|....|....|....|....|....|....|....|....|....|....|....|
hTERT     LDTRTLEVQSDYSSYARTSIRASLTFNRGFKAGRNMRRKLFGVLRLKCHSLFLDLQVNS
γ-ins     LDTRTLEVQSDYSSYARTSIRASLTFNRGFKAGRNMRRKLFGVLRLKCHSLFLDLQVNS
Ins-4     LDTRTLEVQSDYSSYARTSIRASLTFNRGFKAGRNMRRKLFGVLRLKCHSLFLDLQVNS
```

FIG. 2

```
             1003      1013      1023      1033      1043      1053
         ...|....|....|....|....|....|....|....|....|....|....|....|
hTERT    QTVCTNIYKILLLQAYRFHACVLQLPFHQQVWKNPTFFLRVISDTASLCYSILKAKNAG
γ-ins    QTVCTNIYKILLLQAYRFHACVLQLPFHQQVWKNPTFFLRVISDTASLCYSILKAKNAS
Ins-4    QTVCTNIYKILLLQAYRFHACVLQLPFHQQVWKNPTFFLRVISDTASLCYSILKAKNAG 1063      1073      1083      1093      1103      1113
         ...|....|....|....|....|....|....|....|....|....|....|....|
hTERT    SLGAKGAAGPLPSEAVQWLCHQAFLLKLTRHRVTYVPLLGSLRTAQTQLSRKLPGTTLT
γ-ins    ENISVVEPAVLGSGQPSMEPPPRPSGVGSFPVSPGRGAGLQL
Ins-4    CRCLASVEAVPACWC 1123
         ...|....|....|....
hTERT    LEAAANPALPSDFKTILD
```

FIG. 2 CONT.

SEQ ID NO: 1        AEENISVVTPAVLGSGQPEMEPPRRPSGVGSFPVSPGRGAGLGL
SEQ ID NO: 2    YSILKAKNAAEENISVVTPAVLGSGQPEMEPPRRPSGVGSFPVSPGRGAGLGL

SEQ ID NO: 3        VAVLWFNFLFKQKPSVSPRG
SEQ ID NO: 4    ARTFRREKRVAVLWFNFLFKQKPSVSPRG

FIG. 3

```
                3074
5'-AACGCAG|CCGAAGAAAACATTTCTGTCGTGACTCCTGCGGTGCTTGGGTCGGGACAGCCAGAGATGG
     T  A  A  K  K  H  I  L  V  V  T  P  A  V  L  G  S  G  Q  P  E  H  E

AGCCACCCCGCAGACCGTCGGTGTGGGCAGCTTTCCGGTGTCTCCTGGGAGGGGAGTTG
 P  P  R  R  P  S  G  V  G  S  P  P  V  S  P  G  R  G  V  G
                                                     3075
GGCTGGGCCTGTGACTCCTCAGCCTCTGTTTTCCCCCAG|GGATGTC-3'
 L  G  L  *
```

FIG. 4

```
         Exon 4    Intron 4 (bp1-35)        Intron 4          Exon 5
INS1    AAGAGG  |gtggc..//..cagaa|  |gtgcgtt..//..ccgcag|  GCCGAGCGTC Exon 14         Intron 14         Intron 14 (bp 622-781)   Exon 15
INS3    AAGAACGCAG  |gtatgtg..//..gagag|  |ccgaa..//..cccag|   GGATGTC
```

FIG. 5

SEQUENCE LISTING

<160> NUMBER OF SEQ ID NOS: 11

<210> SEQ ID NO 1
<211> LENGTH: 44
<212> TYPE: PRT
<213> ORGANISM: Homo sapiens

<400> SEQUENCE: 1

Ala Glu Glu Asn Ile Ser Val Val Thr Pro Ala Val Leu Gly Ser Gly
1               5                   10                  15

Gln Pro Glu Met Glu Pro Pro Arg Arg Pro Ser Gly Val Gly Ser Phe
            20                  25                  30

Pro Val Ser Pro Gly Arg Gly Ala Gly Leu Gly Leu
        35                  40

<210> SEQ ID NO 2
<211> LENGTH: 53
<212> TYPE: PRT
<213> ORGANISM: Homo sapiens

<400> SEQUENCE: 2

Tyr Ser Ile Leu Lys Ala Lys Asn Ala Ala Glu Glu Asn Ile Ser Val
1               5                   10                  15

Val Thr Pro Ala Val Leu Gly Ser Gly Gln Pro Glu Met Glu Pro Pro
            20                  25                  30

Arg Arg Pro Ser Gly Val Gly Ser Phe Pro Val Ser Pro Gly Arg Gly
        35                  40                  45

Ala Gly Leu Gly Leu
    50

<210> SEQ ID NO 3
<211> LENGTH: 20
<212> TYPE: PRT
<213> ORGANISM: Homo sapiens

<400> SEQUENCE: 3

Val Ala Val Leu Trp Phe Asn Phe Leu Phe Lys Gln Lys Pro Ser Val
1               5                   10                  15

Ser Pro Arg Gly
            20

<210> SEQ ID NO 4
<211> LENGTH: 29
<212> TYPE: PRT
<213> ORGANISM: Homo sapiens

<400> SEQUENCE: 4

Ala Arg Thr Phe Arg Arg Glu Lys Arg Val Ala Val Leu Trp Phe Asn
1               5                   10                  15

Phe Leu Phe Lys Gln Lys Pro Ser Val Ser Pro Arg Gly
            20                  25

<210> SEQ ID NO 5
<211> LENGTH: 9
<212> TYPE: PRT
<213> ORGANISM: Homo sapiens

<400> SEQUENCE: 5

Phe Leu Phe Lys Gln Lys Pro Ser Val
1               5

```
<210> SEQ ID NO 6
<211> LENGTH: 18
<212> TYPE: PRT
<213> ORGANISM: Homo sapiens

<400> SEQUENCE: 6

Arg Val Ala Val Leu Trp Phe Asn Phe Leu Phe Lys Gln Lys Pro Ser
1               5                   10                  15

Val Ser

<210> SEQ ID NO 7
<211> LENGTH: 23
<212> TYPE: DNA
<213> ORGANISM: Homo sapiens

<400> SEQUENCE: 7
gcctccctct gctactccat cct                                           23

<210> SEQ ID NO 8
<211> LENGTH: 27
<212> TYPE: DNA
<213> ORGANISM: Homo sapiens

<400> SEQUENCE: 8
cgtctagagc cggacactca gccttca                                       27

<210> SEQ ID NO 9
<211> LENGTH: 22
<212> TYPE: DNA
<213> ORGANISM: Homo sapiens

<400> SEQUENCE: 9
gccaagttcc tgcactggct ga                                            22

<210> SEQ ID NO 10
<211> LENGTH: 26
<212> TYPE: DNA
<213> ORGANISM: Homo sapiens

<400> SEQUENCE: 10
gctctagaac agtgccttca ccctcg                                        26

<210> SEQ ID NO 11
<211> LENGTH: 21
<212> TYPE: PRT
<213> ORGANISM: Homo sapiens

<400> SEQUENCE: 11

Arg Val Ala Val Leu Trp Phe Asn Phe Leu Phe Lys Gln Lys Pro Ser
1               5                   10                  15

Val Ser Pro Arg Gly
            20
```

POLYPEPTIDES

The present application is a divisional of application Ser. No. 10/451,050, filed Jun. 19, 2003, which is a 371 of PCT/NO01/00498, filed Dec. 18, 2001, the entire contents of which are incorporated herein by reference.

The present invention relates to polypeptides, and nucleic acids DNA encoding these polypeptides, capable of eliciting an immune reaction against cancer, methods for generating T lymphocytes capable of recognising and destroying tumour cells, and pharmaceutical compositions for the treatment, prophylaxis or diagnosis of cancer.

Cancer develops through a multistep process involving several mutational events. These mutations result in altered expression/function of genes belonging to two categories: oncogenes and tumour suppressor genes. Oncogenes arise in nature from proto-oncogenes through point mutations or translocations, thereby resulting in a transformed state of the cell harbouring the mutation. Oncogenes code for and function through a protein. Proto-oncogenes are normal genes of the cell which have the potential of becoming oncogenes. In the majority of cases, proto-oncogenes have been shown to be components of signal transduction pathways. Oncogenes act in a dominant fashion. Tumour-suppressor genes on the other hand, act in a recessive fashion, i.e. through loss of function, and contribute to oncogenesis when both alleles encoding the functional protein have been altered to produce non-functional gene products.

In the field of human cancer immunology, the last two decades have seen intensive efforts to characterise genuine cancer specific antigens. In particular, effort has been devoted to the analysis of antibodies to human tumour antigens. The prior art suggests that such antibodies can be used for diagnostic and therapeutic purposes, for instance in connection with an anti-cancer agent. However, antibodies can only bind to tumour antigens that are exposed on the surface of tumour cells. For this reason, the effort to produce a cancer treatment based on the immune system of the body has been less successful than anticipated.

A fundamental feature of the immune system is that it can distinguish self from nonself molecules and that it does not normally react against self molecules. It has been shown that rejection of tissues or organs grafted from other individuals is an immune response to the foreign antigens on the surface of the grafted cells. The immune response comprises a humeral response, mediated by antibodies, and a cellular response. Antibodies are produced and secreted by B lymphocytes, and typically recognise free antigen in native conformation. They can therefore potentially recognise almost any site exposed on the antigen surface. In contrast to antibodies, T cells, which mediate the cellular arm of the immune response, recognise antigens only in the context of major histocompatability complex (MHC) molecules, and only after appropriate antigen processing. This antigen processing usually consists of proteolytic fragmentation of the protein, resulting in polypeptides that fit into the groove of the to MHC molecules. This enables T cells to also recognise polypeptides derived from intracellular protein fragments/antigens.

T cells can recognise aberrant polypeptides derived from anywhere in the tumour cell, in the context of MHC molecules on the surface of the tumour cell. The T cells can subsequently be activated to eliminate the tumour cell harbouring the aberrant polypeptide. In experimental models involving murine tumours it has been shown that point mutations in intracellular "self" proteins may give rise to tumour rejection antigens, consisting of polypeptides differing in a single amino acid from the normal polypeptide. The T cells recognising these polypeptides in the context of MHC molecules on the surface of the tumour cells are capable of killing the tumour cells and thus rejecting the tumour from the host (Boon et al., 1989, Cell 58: 293-303).

MHC molecules in humans are normally referred to as HLA (human leukocyte antigen) molecules. There are two principal classes of HLA molecules: class I and class II. HLA class I molecules are encoded by HLA A, B and C subloci and primarily activate CD8+ cytotoxic T cells. HLA class II molecules, on the other hand, primarily activate CD4+ (cytotoxic or helper) T cells, and are encoded by the HLA DR, DP and DQ subloci. Every individual normally has six different HLA class I molecules, usually two alleles from each of the three subgroups A, B and C, although in some cases the number of different HLA class I molecules is reduced due to the occurrence of the same HLA allele twice. For a general review, see Roitt, I. M. et al. (1998) *Immunology*, 5$^{th}$ Edition, Mosby, London.

The HLA gene products are highly polymorphic. Different individuals express distinct HLA molecules that differ from those found in other individuals. This explains the difficulty of finding HLA matched organ donors in transplantations. The significance of the genetic variation of the HLA molecules in immunobiology lies in their role as immune-response genes. Through their polypeptide binding capacity, the presence or absence of certain HLA molecules governs the capacity of an individual to respond to specific polypeptide epitopes. As a consequence, HLA molecules influence resistance or susceptibility to disease.

T cells may inhibit the development and growth of cancer by a variety of mechanisms. Cytotoxic T cells, both HLA class I restricted CD8+ and HLA class II restricted CD4+, may directly kill tumour cells presenting the appropriate tumour antigens. Normally, CD4+ helper T cells are needed for cytotoxic CD8+ T cell responses, but if the polypeptide antigen is presented by an appropriate APC, cytotoxic CD8+ T cells can be activated directly, which results in a quicker, stronger and more efficient response.

In International Application PCT/N092/00032 (published as WO92/14756), synthetic polypeptides and fragments of oncogene protein products which have a point of mutation or translocations as compared to their proto-oncogene or tumour suppressor gene protein are described. These polypeptides correspond to, completely cover or are fragments of the processed oncogene protein fragment or tumour suppressor gene fragment as presented by cancer cells or other antigen presenting cells, and are presented as a HLA-polypeptide complex by at least one allele in every individual. The polypeptides were shown to induce specific T cell responses to the actual oncogene protein fragment produced by the cell by processing and presented in the HLA molecule. In particular, it is described in WO92/14756 that polypeptides derived from the p21-ras protein which had point mutations at particular amino acid positions, namely positions 12, 13 and 61. These polypeptides have been shown to be effective in regulating the growth of cancer cells in vitro. Furthermore, the polypeptides were shown to elicit CD4+ T cell immunity against cancer cells harbouring the mutated p21-ras oncogene protein through the administration of such polypeptides in vaccination or cancer therapy schemes. It has subsequently been shown that these polypeptides also elicit CD8+ T cell immunity against cancer cells harbouring the mutated p21 ras oncogene protein through the administration mentioned above (Gjertsen, M. K. et al., 1997, Int. J Cancer 72: 784-790).

International Application PCT/NO99/00143 (published as WO99/58552) describes synthetic polypeptides and fragments of mutant protein products arising from frameshift mutations occurring in genes in cancer cells. These polypeptides correspond to, completely cover or are fragments of the processed frameshift mutant protein fragment as presented by cancer cells or other antigen presenting cells, and are presented as a HLA-polypeptide complex by at least one allele in every individual. In particular polypeptides resulting from frameshift mutations in the BAX and hTGF -RII genes are disclosed. These polypeptides were shown to be effective in stimulating CD4+ and CD8+ T cells in a specific manner.

However, the polypeptides described above will be useful only in certain numbers of cancers involving oncogenes with point mutations, frameshift mutations or translocation in a proto-oncogene or tumour suppressor gene. There is a strong need for an anticancer treatment or vaccine that will be effective against a generic range of cancers.

The concerted action of a combination of altered oncogenes and tumour-suppressor genes results in cellular transformation and development of a malignant phenotype. Such cells are however prone to senescence and have a limited life-span. In most cancers, immortalisation of the tumour cells requires the turning on of an enzyme complex called telomerase. In somatic cells, the catalytic subunit of the telomerase holoenzyme, hTERT (human telomerase reverse transcriptase), is not normally expressed. Additional events, such as the action of proteins encoded by a tumour virus or demethylation of silenced (methylated) promoter sites, can result in expression of the genes encoding the components of the functional telomerase complex in tumour cells.

Due to the presence of telomerase in most types of cancer cells, the enzyme has been disclosed as a general cancer vaccine candidate (International Patent Application No. PCT/NO99/00220, published as WO00/02581). WO00/02581 describes a method for preventing or treating cancer by generating a T cell response against telomerase-expressing cells in a mammal suffering (or likely to suffer from) cancer. It is demonstrated in WO00/02581 that both CD4+ and CD8+ T cells can be stimulated by administration of polypeptides having sequences derived from such a telomerase protein.

Alternative splice variants of the telomerase pre-mRNA have been reported in the literature (Kilian, A. et al, 1997, Hum. Mol. Genet. 6: 2011-2019). Kilian et al. (1997, supra) indicated that it was noteworthy that several splice variants were located with the critical RT (reverse transcriptase) domain of hTERT. They stated, however, that a full understanding of the significance of the hTERT splice variants was not obtained and that further functional characterisation was required.

Analysis of the complete genomic sequence of the hTERT gene, has verified that the different mRNA splice variants arise from the usage of alternative splice sites in the hTERT pre-mRNA (Wick, M. et al., 1999, Gene 232: 97-106). Compared with the full-length hTERT mRNA, at least five additional splice variants have been detected. A schematic drawing of these variants are provided in FIG. 1, and FIG. 2 shows an alignment of the proteins encoded. Two of the splice variants, named -del (or DEL1) and -del (or DEL2), represent deletions of specific coding sequences The -del variant has deleted the first 36 nucleotides of exon 6 and encodes a protein which lacks a stretch of 12 internal amino acids. In the -del variant 182 nucleotides representing the entire exons 7 and 8 are missing, leading to a shift in the open reading frame and a truncated protein with a 44-amino acid long carboxyl terminus not present in the full-length hTERT protein. The remaining splice variants result from the use of alternative splice sites located inside intron regions, resulting in the insertion of intron sequences within the open reading frame and premature termination of translation. The -insert (or INS1) variant results from an insertion of the first 38 nucleotides of intron 4. The -insert does not contain a stop codon, but instead, the open reading frame extends 22 nucleotides into the normal sequence using an alternative reading frame. The -insert (or INS3) variant is caused by insertion of the last 159 nucleotides from intron 14. Ins-4 contains the first 600 nucleotides from intron 14 while at the same time having deleted exon 15 and most of exon 16. The truncated proteins resulting from translation of these splice variants are shown in FIG. 2.

Several recent studies have addressed the regulation of telomerase activity, and some correlation between hTERT mRNA transcription and telomerase activity has been reported for several cell lines and tissues (Nakamura, T. M. et al., 1997, Science 277: 955-959; Meyerson, M. et al, 1997, Int. J. Cancer 85: 330-335; Nakayama, J. et al., 1998, Nature Genet. 18: 65-68; Liu, K. et al., 1999, Proc. Natl Acad. Sci. USA 96: 5147-5152). Others studies have shown that telomerase activity is up-regulated through phosphorylation of the hTERT protein by protein kinase C , and conversely, down-regulated by the presence of protein kinase C inhibitors and phosphatase 2A (Li, H. et al., 1997, J. Biol. Chem. 272: 16729-16732; Li, H. et al., 1998, J. Biol. Chem. 273: 33436-33442; Bodnar, A. G. et al, 1996, Exp. Cell Res. 228: 58-64; Ku, W. C. et al, 1997, Biochem. Biophys. Res. Comm. 241: 730-736). Alternative splicing of the hTERT pre-mRNA represents an additional mechanism for regulating telomerase activity, and has been shown to mediate down-regulation during fetal kidney development and in adult ovarian and uterine tissues (Ulaner, G. A. et al, 1998, Cancer Res. 58: 4168-4172; Ulaner, G. A. et al., 2000, Int. J. Cancer 85: 330-335). The focus of the abovementioned studies has been on the and splice variants, presumably because they delete sequences which are believed to encode critical reverse transcriptase motifs (Lingner, J. et al., 1997, Science 276: 561-567).

The present invention provides peptides and nucleic acids encoding said peptides based on the TERT and splice variants, and the novel use of these peptides and nucleic acids in medicine.

Thus according to the present invention there is provided a polypeptide for use in medicine; wherein the polypeptide:
a) comprises a sequence given in SEQ ID NO: 1, 2, 3, 4, 5, 6 or 11;
b) comprises 8 contiguous amino acids from SEQ ID NO: 1, 2, 3, 4, 5, 6 or 11, with the proviso that at least one of said 8 contiguous amino acids is from SEQ ID NO: 1, 3, 5 or 11; or
c) comprises 8 contiguous amino acids that have only one, two or three amino acid changes (eg. substitutions) relative to the 8 contiguous amino acids as described in b) above, with the proviso that that at least one of the 8 contiguous amino acids present is from SEQ ID NO: 1, 3, 5 or 11;

wherein the polypeptide is capable of inducing a T cell response.

The term "comprises" used herein includes "consists". The polypeptide (or nucleic acid) of the present invention may be flanked by one or more amino acid (or nucleic acid) residues unless otherwise specified. For example, the polypeptide may be part of a fusion protein which has one or more flanking domain at the N- or C-terminus to allow for purification of the fusion protein.

Amino acid changes or modifications (eg. substitutions) in the polypeptide may in particular be made to the anchor residues which fit into HLA or MHC molecules for presentation to T cells. Enhanced binding and immunogenic properties of the polypeptide to HLA or MHC molecules may thus be achieved (see Bristol, J. A. et al., 1998, J. Immunol. 160(5): 2433-2441; Clay, T. M. et al., 1999, J. Immunol. 162(3): 1749-1755).

The polypeptide described above optionally may:
a) have at least 55% sequence identity with a molecule comprising the sequence of SEQ ID NO: 1, as determined by an NCBI BLASTP Version 2.1.2 search with default parameters;
b) have at least 55% sequence identity with a molecule comprising the sequence of SEQ ID NO: 2, as determined by an NCBI BLASTP Version 2.1.2 search with default parameters;
c) have at least 40% sequence identity with a molecule comprising the sequence of SEQ ID NO: 3, as determined by an NCBI BLASTP Version 2.1.2 search with an Expect value of 1000 and other parameters as default;
d) have at least 40% sequence identity with a molecule comprising the sequence of SEQ ID NO: 4, as determined by an NCBI BLASTP Version 2.1.2 search with an Expect value of 1000 and other parameters as default;
e) have at least 70% sequence identity with a molecule comprising the sequence of SEQ ID NO: 5, as determined by an NCBI BLASTP Version 2.1.2 search with an Expect value of 100000 and other parameters as default;
f) have at least 50% sequence identity with a molecule comprising the sequence of SEQ ID NO: 6, as determined by an NCBI BLASTP Version 2.1.2 search with an Expect value of 10000 and other parameters as default; or
g) have at least 40% and preferably 60% sequence identity with a molecule comprising the sequence of SEQ ID NO: 11, as determined by an NCBI BLASTP Version 2.1.2 search with an Expect value of 1000 and other parameters as default;

The NCBI BLASTP program can be found at http://www.ncbi.nlm.nih.gov/blast/, and default parameters changed using the Advanced Search. Higher than default "Expect" values may be required when searching with small query sequences for matches to be displayed: The term "sequence identity" used herein refers to amino acid residues in optimally aligned sequences which match exactly at corresponding relative positions. For example, the NCBI BLASTP program provides a percentage value of identities between query and subject ("hit") sequences.

The polypeptide described above may comprise a sequence as given in SEQ ID NO: 1, 2, 3, 4, 5, 6 or 11 or may be a fragment of a sequence as shown in SEQ ID NO: 1, 3, 5, 6 or 11.

While the polypeptides that are presented by HLA class II molecules are of varying length (12-25 amino acids), the polypeptides presented by HLA class I molecules must normally be nine amino acid residues long in order to fit into the class I HLA binding groove. A longer polypeptide will not bind if it cannot be processed internally by an APC or target cell, such as a cancer cell, before presenting in the class I restricted HLA groove. Only a limited number of deviations from this requirement of nine amino acids have been reported, and in those cases the length of the presented polypeptide has been either eight or ten amino acid residues long. For reviews on polypeptide binding to MHC molecules see Rammensee, H.-G. et al. (1995) Immunogenetics 41: 178-228 and Barinaga (1992), Science 257: 880-881. Male, D. K. et al. (1996, *Advanced Immunology*, Mosby, London) provide background information on the field of immunology.

The T cell response generated by the polypeptide described above may be generated after intracellular cleavage of the polypeptide to provide a fragment that fits into an MHC or HLA binding groove. Alternatively, the polypeptide described above may not need intracellular cleavage to fit into an MHC or HLA class I binding groove. In this case, the polypeptide may be from 8 to 10 amino acids long. Also provided is a polypeptide described above which does not need intracellular cleavage to fit into an MHC or HLA class II binding groove. In this case, the polypeptide may be from 12 to 25 amino acids long.

The T cell response according to the present invention may increase the number and/or activity of T helper and/or T cytotoxic cells.

Also provided is a polypeptide which does not stimulate a substantial cytotoxic T cell response in a patient against one or more of the following: bone marrow stem cells, epithelial cells in colonic crypts or lymphocytes.

Further provided according to the present invention is a nucleic acid molecule for use in medicine; wherein the nucleic acid molecule:
a) has a strand that encodes a polypeptide described above, as described above;
b) has a strand that is complementary with a strand as described in a) above; or
c) has a strand that hybridises with a molecule as described in a) or b) above (eg. under stringent conditions).

Stringent hybridisation conditions are discussed in detail at pp 1.101-1.110 and 11.45-11.61 of Sambrook, J. et al. (1989, Molecular Cloning, 2nd Edition, Cold Spring Harbor Laboratory Press, Cold Spring Harbor). One example of hybridisation conditions that can be used involves using a pre-washing solution of 5×SSC, 0.5% SDS, 1.0 mM EDTA (pH 8.0) and attempting hybridisation overnight at 55° C. using 5×SSC. Hybridising nucleic acid sequences within the scope of the present invention include probes, primers or DNA fragments. The term primer includes a single stranded oligonucleotide which acts as a point of initiation of template-directed DNA synthesis under appropriate conditions (eg. in the presence of four different nucleoside triphosphates and an agent for polymerisation, such as DNA or RNA polymerase or reverse transcriptase) in an appropriate buffer and at a suitable temperature.

Also provided is a vector or cell for use in medicine comprising a nucleic acid molecule according to the present invention.

Further provided is a binding agent for use in medicine; wherein the binding agent binds to a polypeptide described above as described above. Said binding agent may be specific for a polypeptide as described above. Said binding agent may be an antibody or a fragment thereof. Said binding agent may be lectin.

The term antibody in its various grammatical forms is used herein to refer to immunoglobulin molecules and immunologically active portions of immunoglobulin molecules, i.e., molecules that contain an antibody combining site or paratope. Such molecules are also referred to as "antigen binding fragments" of immunoglobulin molecules. Illustrative antibody molecules are intact immunoglobulin molecules, substantially intact immunoglobulin molecules and those portions of an immunoglobulin molecule that contain the paratope, including those portions known in the art as Fab, Fab', F(ab')2 and F(v). Antibodies of the present invention may be monoclonal or polyclonal. The term antibody is also intended to encompass single chain antibodies, chimeric, humanised or primatised (CDR-grafted) antibodies and the like, as well as chimeric or CDR-grafted single chain antibodies, comprising portions from two different species. For preparation of antibodies see Harlow, E. and Lane, D. (1988, *Antibodies: A Laboratory Manual*, Cold Spring Harbor Laboratory Press, Cold Spring Harbor) and Harlow, E. and Lane, D. (1999, *Using Antibodies: A Laboratory Manual*, Cold Spring Harbor Laboratory Press, Cold Spring Harbor). Immunological adjuvants for vaccines comprising lecithin may be used to stimulate antibody production (see for example U.S. Pat. No. 4,803,070).

Further provided according to the present invention is a T lymphocyte for use in medicine; wherein the T lymphocyte is capable of killing a cell expressing a polypeptide described above according to the present invention or of helping in the killing of such a cell. Said T lymphocyte may be a T cytotoxic cell or a T helper cell.

Also provided is a clonal cell line for use in medicine comprising a plurality of T lymphocytes as described above. Also provided is a mixture of T lymphocytes for use in medicine comprising a T helper cell or a clonal cell line of such cells and a T cylotoxic cell or a clonal cell line of such cells.

Also provided is a method of generating T lymphocytes capable of recognising and destroying tumour cells in a mammal, comprising taking a sample of T lymphocytes from a mammal and culturing the T lymphocyte sample in the presence of at least one polypeptide described above in an amount sufficient to generate hTERT -insert protein specific T lymphocytes and/or hTERT -insert protein specific T lymphocytes.

Also provided is a B lymphocyte which may be useful in generating antibodies according to the present invention. Hybridomas which are capable of generating antibodies according to the present invention are also included (see for example Koehler et al., 1975, Nature 256: 495-497; Kosbor et al., 1983, Immunol. Today 4: 72; Cote et al., 1983, PNAS USA 80: 2026-2030; Cole et al., 1985, *Monoclonal Antibodies and Cancer Therapy*, Alan R. Liss Inc., New York, pp. 77-96)

Further provided according to the present invention is the use of a polypeptide as described above, a nucleic acid as described above, a vector or cell as described above, a binding agent as described above, a T lymphocyte as described above, a cell line as described above, or a mixture of T lymphocytes as described above, in the preparation of a medicament for treating cancer, or in the preparation of a diagnostic for diagnosing cancer. The cancer may be a mammalian cancer. In particular, the cancer may be human cancer. For example, the cancer may be breast cancer, prostate cancer, pancreatic cancer, colo-rectal cancer, lung cancer, malignant melanoma, leukaemia, lymphoma, ovarian cancer, cervical cancer or a biliary tract carcinoma.

Said medicament may be a vaccine.

The polypeptides described here are particularly suited for use in a vaccine capable of safely eliciting either CD4+ or CD8+ T cell immunity. As the polypeptides may be synthetically produced, medicaments including the polypeptides do not include transforming cancer genes or other sites or materials which might produce deleterious effects. The polypeptides may be targeted for a particular type of T cell response without the side effects of other unwanted responses.

Said medicament may be an antisense molecule or is capable of generating an antisense molecule in vivo.

Said diagnostic may be provided in a kit. The kit may comprise means for generating a detectable signal (eg. a fluorescent label, a radioactive label) or a detectable change (eg. an enzyme-catalysed change). The kit may include instructions for use in diagnosing cancer.

Further provided is a pharmaceutical composition comprising a polypeptide as described above, a nucleic acid as described above, a vector or cell as described above, a binding agent as described above, a T lymphocyte as described above, a cell line as described above, or a mixture of T lymphocytes as described above.

Said pharmaceutical composition may comprise a polypeptide capable of inducing a T cell response directed against a polypeptide produced by an oncogene or against a mutant tumour suppressor protein, or a nucleic acid encoding such a polypeptide, or a binding agent that binds such a polypeptide, or a T cell that is capable of killing a cell expressing such a polypeptide or of helping in the killing of such a cell. Example of such oncogenes or mutant tumour suppressor proteins include p21-ras, Rb, p53, abl, gip, gsp, ret or trk. The oncogene target may be the p21-ras polypeptides described in International Application No. PCT/NO92/00032 (Publication No. WO92/14756).

Also provided is a combined preparation comprising a component from the pharmaceutical compositions described above for simultaneous, separate or sequential use in anti-cancer therapy.

Also provided is a pharmaceutical composition or a combined preparation as described above further comprising a pharmaceutically acceptable carrier, diluent, additive, stabiliser, and/or adjuvant; said composition or combined preparation optionally further including one or more of: a cytokine or growth factor (eg. IL-2, IL-12, and/or GM-CSF) and another polypeptide arising from a frameshift mutation (eg. a frameshift mutation in the BAX or hTGFβ-RII gene.)

The stimulatory effect on CD4+ and CD8+ T cells in a specific manner by polypeptides resulting from frameshift mutations in the BAX and hTGF -RII genes was disclosed in WO99/58552 (see above).

The pharmaceutical composition or combined preparation described above may be a vaccine.

The pharmaceutical composition or combined preparation described above may comprise or be capable of producing antisense molecules.

Also provided is a method for the preparation of a pharmaceutical composition as described above, comprising the steps of combining the above described components with a pharmaceutically acceptable carrier, diluent, additive, stabiliser and/or adjuvant.

A pharmaceutical composition according to the present may comprise any of the following mixtures:

a) a mixture of at least one polypeptide described above together with another polypeptide having a different sequence;
  b) a mixture of at least one polypeptide described above together with another polypeptide having an overlapping sequence, so that the polypeptides are suitable to fit different MHC or HLA alleles;
  c) a mixture of both mixtures a) and b);
  d) a mixture or several mixtures a);
  e) a mixture of several mixtures b); or
  f) a mixture of several mixtures a) and several mixtures b).

The polypeptides in the mixture may be covalently linked with each other to form larger polypeptides or even cyclic polypeptides. The polypeptides themselves may be in a linear or cyclic form.

Also provided according to the present invention is a diagnostic composition comprising a polypeptide as described above, a nucleic acid as described above, a vector or cell as described above, a binding agent as described above, a T lymphocyte as described above, a cell line as described above, or a mixture of T lymphocytes above.

Also provided according to the present invention is a diagnostic kit as described above.

Also provided according to the present invention is a method of treatment or prophylaxis of cancer of the human or animal body comprising administering a therapeutically effective amount of pharmaceutical composition described above to a patient or animal in need of same. The invention includes a method of treatment or prophylaxis of patient or animal afflicted with cancer, the method comprising administering to said patient or animal a pharmaceutical composition described above in an amount sufficient to elicit a T-cell response against said cancer. The method of treatment may also include stimulation in vivo or ex vivo with a pharmaceutical composition described above. Ex vivo therapy may include isolating dendritic cells or other suitable antigen presenting cells from a patient or animal, loading said cells with at least one polypeptide or nucleic acid described above, and infusing these loaded cells back into the patient or animal. The polypeptides or nucleic acids described above may also be used in a method of vaccination of a patient in order to obtain resistance against cancer. Oncogenes are sometimes associated with viruses. The present invention is also suitable for the treatment of certain viral disorders.

The polypeptides according to the present invention may be administered in an amount in the range of 1 microgram (1 g) to 1 gram (1 g) to an average human patient or individual to be vaccinated. It is preferred to use a smaller dose in the range of 1 microgram (1 g) to 1 milligram (1 mg) for each administration.

The exact dosages, ie. pharmaceutically acceptable dosages, and administration regime of pharmaceutical compositions and medicaments of the present invention may be readily determined by one skilled in the art, for example by using for example dose-response assays.

The administration may take place one or several times as suitable to establish and/or maintain the desired T cell immunity. The polypeptides according to the present invention may be administered together, either simultaneously or separately, with compounds such as cytokines and/or growth factors, i.e., interleukin-2 (IL-2), interleukin-12 (IL-12), granulocyte macrophage colony stimulating factor (GM-CSF) or the like in order to strengthen the immune response as known in the art. The polypeptides can be used in a vaccine or a therapeutic composition either alone or in combination with other materials. For example, the polypeptide or polypeptides may be supplied in the form of a lipopeptide conjugate which is known to induce a high-affinity cytotoxic T cell response (Deres, K. et al., 1989, Nature 342: 561-564).

The polypeptides according to the present invention may be administered to an individual or animal in the form of DNA vaccines. The DNA encoding the polypeptide(s) may be in the form of cloned plasmid DNA or synthetic oligonucleotide. The DNA may be delivered together with cytokines, such as IL-2, and/or other co-stimulatory molecules. The cytokines and/or co-stimulatory molecules may themselves be delivered in the form of plasmid or oligonucleotide DNA.

Response to a DNA vaccine has been shown to be increased by the presence of immunostimulatory DNA sequences (ISS). These can take the form of hexameric motifs containing methylated CpG, according to the formula: 5'-purine-purine-CG-pyrimidine-pyrimidine-3'. DNA vaccines according to the present invention may therefore incorporate these or other ISS, in the DNA encoding the hTERT -insert protein and/or the hTERT -insert protein, in the DNA encoding the cytokine or other co-stimulatory molecules, or in both. A review of the advantages of DNA vaccination is provided by Tighe et al. (1998, Immunology Today, 19(2): 89-97).

Also provided according to the present invention is the polypeptide as described above, optionally in isolated form, wherein the polypeptide is not a polypeptide consisting of the sequences shown in FIG. 4.

The polypeptide sequence shown in FIG. 4 represents the disclosure in FIG. 5C of Kilian et al. (1997, supra) of 46 amino acid residues at the C-terminal end of the circa 1100 amino acid residue hTERT -insert splice variant, which includes 44 amino acids of SEQ ID NO: 1. The sequence provided in Kilian et al. (1997, supra) shows the "alternative C-termninus" of the hTERT -insert splice variant protein. (Kilian et al., 1997, supra, indicate that the corresponding DNA sequence in provided by GenBank Accession number AF015950.) Kilian et al. (1997, supra) do not disclose as a separate entity the polypeptide according to SEQ ID NOs: 1, 2 or 5 at the C-terminal end of the hTERT -insert splice variant protein, and they do not disclose or suggest medicinal use of the polypeptide according to SEQ ID NO: 1, 2 or 5.

The polypeptides described herein may be produced by conventional processes, for example, by the various polypeptide synthesis methods known in the art. Alternatively, they may be fragments of a hTERT -insert protein and/or a hTERT -insert protein produced by cleavage, for example, using cyanogen bromide, and subsequent purification. Enzymatic cleavage may also be used. The hTERT -insert protein and the hTERT -insert protein or peptides may also be in the form of recombinant expressed proteins or polypeptides.

Also provided is the nucleic acid as described herein, optionally in isolated form; wherein the nucleic acid is not a nucleic acid encoding the polypeptide excluded above and is also not a nucleic acid as shown in FIG. 4 or FIG. 5.

The nucleic acid sequence at the 3'-end of the circa 3100 bp hTERT -insert splice variant, part of which encodes the C-terminal end of the corresponding protein that includes SEQ ID NO: 1, is provided in FIG. 4 of Kilian et al. (1997, supra). The nucleic acid sequence at the exon-intron borders of the hTERT splice variants INS1 (equivalent to the -insert splice variant) and INS3 (equivalent to the -insert splice variant), as disclosed in FIG. 2B of Wick et al. (1999, supra), are shown in FIG. 5. The nucleic acids shown in FIG. 5 as disclosed in FIG. 2B of Wick et al. (1999, supra) include nucleotides which encode amino acid residues present in SEQ ID NOs: 1-6 and 11. Wick et al. (1999, supra) make no specific reference to the existence of the nucleic acids shown as distinct entities or to their medical use. Wick et al., 1999, supra, provide reference to the complete nucleotide sequence of their hTERT gene in GenBank Accession numbers AF128893 and AF128894.

Nucleic acids encoding the polypeptides of the present invention may be made by oligonucleotide synthesis. This may be done by any of the various methods available in the art. A nucleic acid encoding telomerase protein may be cloned from a genomic or cDNA library, using conventional library screening. The probe may correspond to a portion of any sequence of a known hTERT -insert and/or hTERT -insert gene. Alternatively, the nucleic acid can be obtained by using the Polymerase Chain Reaction (PCR). The nucleic acid is preferably DNA, and may suitably be cloned into a vector. Subclones may be generated by using suitable restriction enzymes. The cloned or subcloned DNA may be propagated in a suitable host, for example a bacterial host. Alternatively, the host can be a eukaryotic organism, such as yeast or baculovirus. The hTERT -insert and the hTERT -insert proteins or polypeptides may be produced by expression in a suitable host. In this case, the DNA is cloned into an expression vector. A variety of commercial expression kits are available. The methods described in Sambrook, J. et al. (1989, *Molecular Cloning: A Laboratory Manual*, Cold Spring Harbor Laboratory Press, Cold Spring Harbor) may be used for these purposes.

Also provided is the vector or cell as described herein, optionally in isolated form.

Further provided is the binding agent as described herein, optionally in isolated form.

Yet further provided is the T lymphocyte as described herein, optionally in isolated form.

Also provided is the clonal cell line as described herein, optionally in isolated form.

Further provided is the mixture of T lymphocytes as described herein.

Also provided is a machine readable data carrier (eg. a disk) comprising the sequence of a polypeptide or of a nucleic acid as described herein.

Yet further provided is a method comprising using the sequence of a polypeptide or a nucleic acid molecule as described herein to perform sequence identity studies, sequence homology studies, or hybridisation studies. Said method may include using said sequence to predict structure and/or function (eg. to predict anti-cancer activity). Also provided is the use of this method in a drug development or screening procedure. Further provided is a drug identified or selected by this procedure.

Also provided is a computer or database that displays or stores a sequence of a polypeptide or a nucleic acid molecule as described herein or that is set up to perform a method as described above.

Also provided is the invention as substantially hereinbefore described with reference to the accompanying figures and examples.

The phrases "amino acid residue" and "amino acid" are broadly defined to include modified and unusual amino acids as defined in WIPO Standard ST.25, and incorporated herein by reference.

The term treatment or therapy used herein includes prophylactic treatment or therapy where applicable.

The contents of each of the references discussed herein, including the references cited therein, are herein incorporated by reference in their entirety.

The invention will be further apparent from the following description, with reference to the several accompanying figures, which show, by way of example only, various polypeptides and their use according to the present invention.

Of the figures:

FIG. 2 shows a protein alignment between a portion of the hTERT protein and proteins resulting from translation of splice variants;

FIG. 3 shows the carboxyl termini of the hTERT -insert and -insert splice variant proteins;

FIG. 4 shows prior art sequences relating to the hTERT -insert splice variant as disclosed in FIG. 5C of Kilian et al. (1997, supra);

FIG. 5 show prior art sequences relating to the hTERT -insert and -insert splice variants as disclosed in FIG. 2B of Wick et al. (1999, supra);

Figure 1:
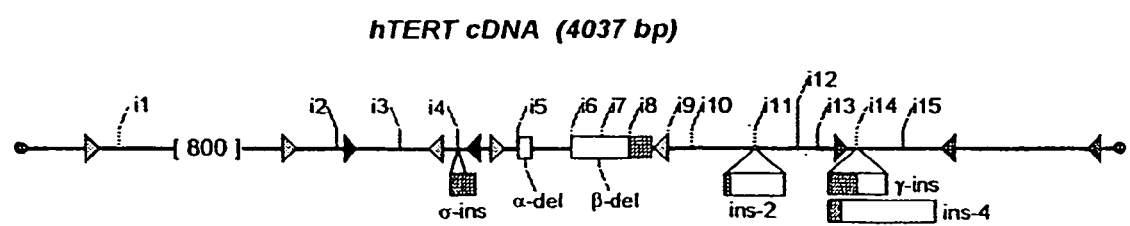
FIG. 1 is a schematic drawing of the full-length hTERT mRNA and splice variants found in cancer cell lines.

In FIG. 1, the position of introns present in the hTERT pre-mRNA is indicated by the letter "i" followed by an appropriate number. Insertion and deletion variants are shown as square boxes; shaded fill represents sequences that encode protein sequence not present in the full-length hTERT protein. Position and orientation of oligonucleotide primers used to analyse the different splice variants is indicated by arrows.

In FIG. 2, amino acid numbering is shown above the sequence. Amino acids are represented by their standard one letter abbreviation known in the art.

In FIG. 3, SEQ ID NO: 1 reflects the truncated tail of the hTERT -insert protein and SEQ ID NO: 2 reflects the same polypeptide with an extension at the amino terminus with the nine amino acids normally found in these positions in the naturally occurring hTERT -insert expression product (underlined). SEQ ID NO: 3 reflects the truncated tail of the hTERT -insert protein. SEQ ID NO: 4 reflects SEQ ID NO: 3 with an extension at the amino terminus with the nine amino acids normally found in these positions in the naturally occurring hTERT -insert expression product (underlined).

In FIG. 4, the exon/intron junctions of insert splice variant 3 (equivalent to the hTERT -insert splice variant) is shown as provided in FIG. 5C of Kilian et al (1997, supra). The following information is provided by Kilian et al. (1997, supra): the nucleic acid sequence is shown above a protein translation sequence, with the putative unspliced intron given in bold type; putative exon/intron junctions are marked with |; the nucleic acid sequence numbering corresponds as follows: nucleotide 1 corresponds to nucleotide 139 of the sequence in GenBank Accession number AF015950; and amino acids corresponding to the putative c-Ab1/SH3 binding site are underlined. The amino acid sequence shown by Kilian et al (1997; supra) represents the C-terminal end of a circa 1100 amino acid residue hTERT -insert splice variant protein.

In FIG. 5, nucleotides of the exon-intron borders of the hTERT splice variants INS1 (equivalent to the -insert splice variant) and INS3 (equivalent to the -insert splice variant), as disclosed in FIG. 2B of Wick et al (1999, supra), are represented. Intronic and exonic sequences are shown in lower-case and upper-case letters, respectively. Wick et al. (1999, supra) indicate that the nucleotide sequence of their hTERT gene has been deposited as GenBank Accession numbers AF128893 and AF128894.

It has been established that the hTERT -insert and -insert splice variants are expressed in cancer cell lines and tumours but are undetectable, or present at very low levels, in nomial cells. The present application therefore discloses general cancer vaccine candidates with improved specificity in comparison with vaccines based on the functional variant of the telomerase (hTERT) protein. Both and inserts results in formation of an early stop codon and the expression of a protein that is truncated at the carboxyl terminus. The truncated hTERT γ- and σ-insert proteins have no telomerase activity themselves. In the case of a -insert the truncated tail of the protein is a sequence of 44 amino acids (SEQ ID NO: 1). A -insert results in a protein in which the truncated tail is a sequence of 20 amino acids (SEQ ID NO: 3). They are predominantly expressed in cancer cell lines but are undetectable, or present at very low levels, in normal cells and are therefore targets for specific immunotherapy. According to the present invention, polypeptides corresponding to the carboxyl end (truncated tail) of proteins expressed by hTERT -insert and/or -insert splice variants, are useful as anticancer agents or vaccines with the function to trigger the cellular arm of the immune system (T-cells) in humans against cancer cells. In a preferred embodiment of the invention, the polypeptide comprises the sequence according to SEQ ID NO: 5. In another preferred embodiment of the invention, the polypeptide comprises the sequence according to SEQ ID NO: 6. It yet another preferred embodiment, the polypeptide comprises the sequence according to SEQ ID NO: 11.

EXPERIMENTAL

The experiments outlined herein describe the characterisation of hTERT splice variants in various cancer cell lines compared with normal cells. Synthesis of polypeptides according to the present invention, and experiments for testing the efficacy of the polypeptides for use in cancer therapy are detailed. An experiment showing induction and proliferation of human T cells by the peptide having an amino acid sequence according to SEQ ID NO: 11 is described.

RT-PCR Analysis of the -Insert and σ-Insert Splice Variants of hTERT

RNA Analysis:

Poly(A)+ mRNA from completely lysed cells was isolated directly from crude lysates using magnetic oligo(dT) beads (Dynal A S; Jakobsen, K. S. et al., 1990, Nucleic Acids Res. 18: 3669). Cytosolic mRNA fractions were prepared by incubating cells in 1% IGEPAL (Sigma) at 0° C. for one minute, followed by centrifugation [10000 g; 1 min.; 4° C.] to remove nuclei. Poly(A)+ mRNA was then isolated from the supernatant using oligo(dT) beads as described above.

cDNA Synthesis and PCR:

First strand cDNA synthesis was carried out by standard procedures using M-MLV RNaseH+ reverse transcriptase (Promega Corp.), and the PCR reactions were performed by using HotStar Taq DNA polymerase (Qiagen) and run for 35 cycles on a PTC-200 thermal cycler (MJ Research). To obtain detectable products from PBM and CD34+ cells, 10% of the reaction was used as template in a second PCR reaction and amplified by 15 additional cycles.

For analysis of the -insert splice variant the plus-strand primer variant the plus-strand primer hTERT-p3195 (5-GCC TCC CTC TGC TAC TCC ATC CT—SEQ ID NO: 7) and minus-strand primer hTERT-m3652 (5-CGT CTA GAG CCG GAC ACT CAG CCT TCA—SEQ ID NO: 8) were used. Applied on the full-length hTERT cDNA and the -insert variant, these primers produce fragments of 465 and 624 nucleotides, respectively. The analysis of the σ-insert variant was performed by using primers hTERT-P6 (5-GCC AAG TAC CTG CAC TGG CTG A—SEQ ID NO: 9) and hTERT-m2044 (5-GCT CTA GAA CAG TGC CTT CAC CCT CG—SEQ ID NO: 10). The amplification product resulting from using these primers with full-length hTERT cDNA and the σ-insert variant comprises 369 and 407 nucleotides, respectively. To verify that these PCR products represent genuine splice variants, the fragments were isolated from the gel and analysed by direct sequencing using an ABI prism 310 automated sequencer (PE Corp.).

Results:

Telomerase activity is subject to complex regulation at the post-transcriptional level, and methods used to detect the presence or absence of telomerase proteins should involve direct measurements of the protein itself, or alternatively, mRNA variants. Furthermore, the abundance of the different hTERT splice variants found in cells is not necessarily correlated with the levels found in the cytosolic fraction of the same cells (see FIG. 6). Such deviations may be explained by differences in the efficiency with which mRNA variants are transported from the nucleus to the cytosolic compartment, and/or by differential stability of the specific splice variants in the cytosol. It is well known in the art that such mechanisms are part of the concept of gene regulation. Nevertheless, the studies conducted to explain hTERT regulation, including those cited above, have used total RNA or mRNA isolated from completely lysed cells for their analysis. Kits and reagents required to perform this kind of RNA isolation are widely available in the commercial market. To obtain a correct picture of gene expression, studies on mRNA abundance should include analysis of mRNA specific t the cytosolic compartment.

Figure 6:
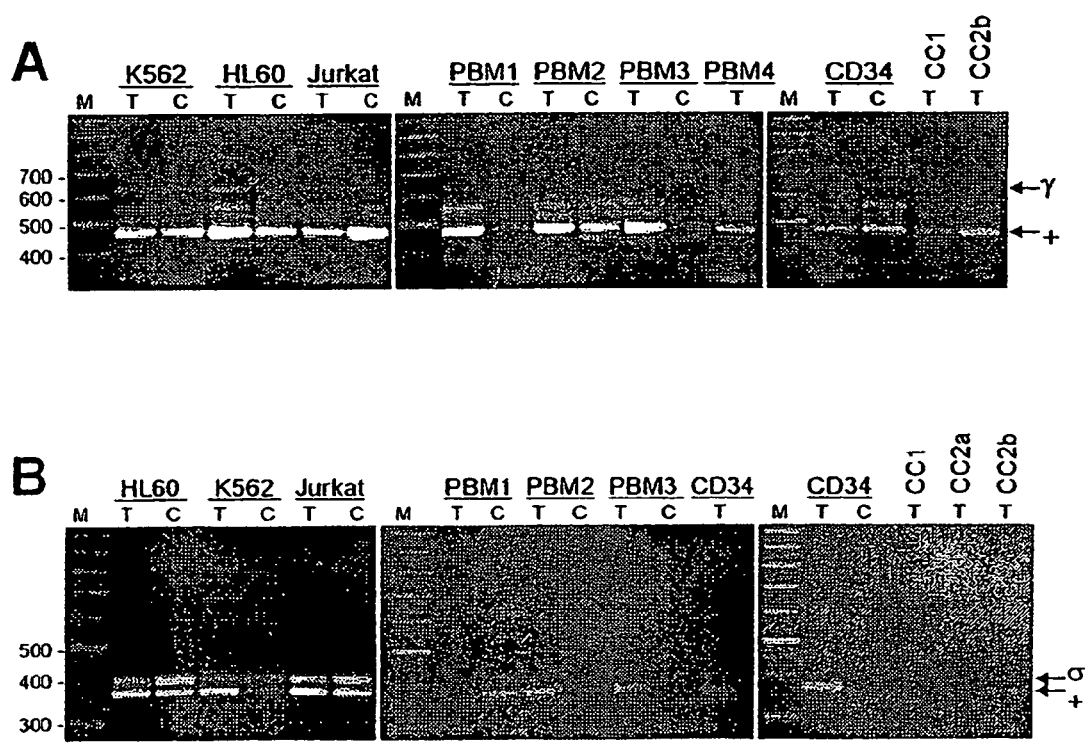
FIG. 6 shows results from RT-PCR analysis of the regions comprising the -insert (A) and σ-insert (B) splice variants of hTERT.

FIG. 6 shows results from RT-PCR analysis of the regions comprising the γ- (A) and. σ-insert variants (B) of hTERT. HL60, K562, and Jurkat denote the cancer cell lines analysed. HL60 is a promyelocytic leukemia cell line (Sokoloski, J. A. et al., 1993, Blood 82: 625-632), K562 an erythroid leukemia cell line (Lozzio, C. B. et al., 1975, Blood 45: 321-324), while Jurkat is derived from acute T-lymphocyte leukemia cells (Gillis, S. et al, 1980, J. Exp. Med. 152: 1709-1719). The HL60, K562, and Jurkat cancer cell lines are commercially available (for example, from ATCC, Oslo). PBM1, PBM2, PBM3 and PBM4 represent peripheral blood mononuclear (PBM) cell populations isolated from four different healthy donors. CD34 denotes CD34-positive stem cells isolated from a healthy donor, and CC1/CC2 denotes colon cancer biopsies obtained from two cancer patients at the Norwegian Radium Hospital, Oslo, with CC2a and CC2b being two tissue samples dissected from the same tumour. RT-PCR reactions performed with mRNA isolated by complete lysis of cells and with mRNA isolated from cytosolic fractions are marked with the letters "T" and "C", respectively. "M" indicates lane with molecular weight marker. Position of PCR fragments representing the γ- and σ-insert splice variants and the respective full-length hTERT products (+) is indicated on the right side of the panels.

The RT-PCR analysis showed that both γ- and σ-insert splice variants were readily detectable in all cancer cell lines and in one of the tumour samples analysed (CC2b), and with the σ-insert variant appearing as the most abundant in cytosolic fractions. In contrast, we were not able to detect these variants in cytosolic mRNA populations isolated from PBM cells despite the extensive PCR amplification performed with these samples. The identity of the weak 395-bp fragment produced with the σ-insert primers on PBM and CD34-positive cells is at present unknown.

Polypeptide Synthesis and Analysis for Applications Relating to Cancer

Polypeptide Synthesis:

The polypeptides were synthesised by using continuous flow solid phase peptide synthesis. N-a-Fmoc-amino acids with appropriate side chain protection were used. The Fmoc-amino acids were activated for coupling as pentafluorophenyl esters or by using either TBTU or diisopropyl carbodiimide activation prior to coupling. 20% piperidine in DMF was used for selective removal of Fmoc after each coupling. Cleavage from the resin and final removal of side chain protection was performed by 95% TFA containing appropriate scavengers. The polypeptides were purified and analysed by reversed phase HPLC. The identity of the polypeptides was confirmed by using electro-spray mass spectroscopy.

Polypeptide Testing and Cancer Therapy:

In order for a cancer vaccine according to the present invention, and methods for specific cancer therapy based on T cell immunity to be effective, two conditions must be met:
(a) the polypeptide is at least 8 amino acids long and is a fragment of the hTERT -insert protein or the hTERT -insert protein and
(b) the polypeptide is capable of inducing, either in its full length or after processing by antigen presenting cell, T cell responses.

The following experimental methods may be used to determine if these two conditions are met for a particular polypeptide. First, it should be determined if the particular polypeptide gives rise to T cell immune responses in vitro. It will also need to be established if the synthetic polypeptides correspond to, or are capable after processing to yield, polypeptide fragments corresponding to polypeptide fragments occurring in cancer cells harbouring the hTERT -insert protein and/or the hTERT -insert protein or antigen presenting cells that have processed naturally occurring hTERT -insert protein and/or hTERT -insert protein. The specificity of T cells induced in vivo by hTERT -insert and/or hTERT -insert polypeptide vaccination may also be determined.

In Vitro T Cell Response Analysis:

It is necessary to determine if hTERT -insert and/or hTERT -insert expressing tumour cell lines can be killed by T cell clones obtained from peripheral blood from carcinoma patients after hTERT -insert and/or hTERT -insert polypeptide vaccination. T cell clones are obtained after cloning of T-cell blasts present in peripheral blood mononuclear cells (PBMC) from a carcinoma patient after hTERT -insert and/or hTERT -insert polypeptide vaccination. The polypeptide vaccination protocol includes several in vivo injections of polypeptides intracutaneously with GM-CSF or another commonly used adjuvant. Cloning of T cells is performed by plating responding T cell blasts at 5 blasts per well onto Terasaki plates. Each well contains $2 \times 10^4$ autologous, irradiated (30 Gy) PBMC as feeder cells. The cells are propagated with the candidate hTERT -insert and/or hTERT -insert polypeptide at 25 mM and 5 U/ml recombinant interleukin-2 (rIL-2) (Amersham, Aylesbury, UK) in a total volume of 20 ml. After 9 days T cell clones are transferred onto flat-bottomed 96-well plates (Costar, Cambridge, Mass.) with 1 mg/ml phytohemagglutinin (PHA, Wellcome, Dartford, UK), 5 U/ml rIL-2 and allogenic irradiated (30 Gy) PBMC ($2 \times 10^5$) per well as feeder cells. Growing clones are further expanded in 24-well plates with PHA/rIL-2 and $1 \times 10^6$ allogenic, irradiated PBMC as feeder cells and screened for polypeptide specificity after 4 to 7 days.

T cell clones are selected for further characterisation. The cell-surface phenotype of the T cell clone is determined to ascertain if the T cell clone is CD4+ or CD8+. T cell clone is incubated with autologous tumour cell targets at different effector to target ratios to determine if lysis of tumour cells occurs. Lysis indicates that the T cell has reactivity directed against a tumour derived antigen, for example, hTERT -insert and/or hTERT -insert proteins.

Correlation Between Polypeptides and in Vivo hTERT Insert Fragments:

In order to verify that the antigen recognised is associated with hTERT -insert protein or hTERT -insert protein, and to identify the HLA class I or class II molecule presenting the putative hTERT -insert or hTERT -insert polypeptide to the T cell clone, different hTERT -insert and/or hTERT -insert expressing turmour cell lines carrying one or more HLA class I or II molecules in common with those of the patient, are used as target cells in cytotoxicity assays. Target cells are labelled with $^{51}$Cr or $^{3}$H-thymidine ($9.25 \times 10^4$ Bq/mL) overnight, washed once and plated at 5000 cells per well in 96 well plates. T cells are added at different effector to target ratios and the plates are incubated for 4 hours at 37° C. and then harvested before counting in a liquid scintillation counter (Packard Topcount). For example, the bladder carcinoma cell line T24 (12Val$^+$, HLA-1$^+$, B35$^+$), the melanoma cell line FMEX (12Val$^+$, HLA-A2$^+$, B35$^+$) and the colon carcinoma cell line SW 480 (12Val$^+$, HLA-A2$^+$, B8$^+$) or any other telomerase positive tumour cell line may be used as target cells. A suitable cell line which does not express hTERT -insert and/or hTERT -insert proteins may be used as a control, and should not be lysed Lysis of a particular cell line indicates that the T cell clone being tested recognises an endogenously-processed hTERT -insert and/or hTERT -insert epitope in the context of the HLA class I or class II subtype expressed by that cell line.

Characterisation of T Cell Clones:

The HLA class I or class II restriction of a T cell clone may be determined by blocking experiments. Monoclonal antibodies against HLA class I antigens, for example the panreactive HLA class I monoclonal antibody W6/32, or against class II antigens, for example, monoclonals directed against HLA class II DR, DQ and DP antigens (B8/11, SPV-L3 and B7/21), may be used. The T cell clone activity against the autologous tumour cell line is evaluated using monoclonal antibodies directed against HLA class I and class II molecules at a final concentration of 10 mg/ml. Assays are set up as described above in triplicate in 96 well plates and the target cells are preincubated for 30 minutes at 37° C. before addition of T cells.

The fine specificity of a T cell clone may be determined using polypeptide pulsing experiments. To identify the hTERT -insert and/or hTERT -insert polypeptide actually being recognised by a T cell clone, a panel of nonamer polypeptides is tested. $^{51}$Cr or $^{3}$H-thymidine labelled, mild acid eluted autologous fibroblasts are plated at 2500 cells per well in 96 well plates and pulsed with the polypeptides at a concentration of 1 mM together with b2-microglobulin (2.5 mg/mL) in a 5% $CO_2$ incubator at 37° C. before addition of the T cells Assays are set up in triplicate in 96 well plates and incubated for 4 hours with an effector to target ratio of 5 to 1. Controls can include T cell clone cultured alone, with APC in the absence of polypeptides or with an irrelevant melanoma associated polypeptide MART-1/Melan-A polypeptide.

An alternative protocol to determine the fine specificity of a T cell clone may also be used. In this alternative protocol, the TAP deficient T2 cell line is used as antigen presenting cells. This cell line expresses only small amounts of HLA-A2 antigen, but increased levels of HLA class I antigens at the cell surface can be induced by addition of b2-microglobulin. $^3$H-labelled target cells are incubated with the different test polypeptides and control polypeptides at a concentration of 1 mM together with b2-microglobulin (2.5 mg/mL) for one hour at 37° C. After polypeptide pulsing, the target cells are washed extensively, counted and plated at 2500 cells per well in 96 well plates before addition of the T cells. The plates are incubated for 4 hours at 37° C. in 5% $CO_2$ before harvesting. Controls include T cell clone cultured alone or with target cells in the absence of polypeptides. Assays were set up in triplicate in 96 well plates with an effector to target ratio of 20 to 1.

The sensitivity of a T cell clone to a particular polypeptide identified above may also be determined using a dose-response experiment Polypeptide sensitised fibroblasts can be used as target cells. The target cells are pulsed with the particular peptide as described above for fine specificity determination, with the exception that the peptides are added at different concentrations before the addition of T cells. Controls include target cells alone and target cells pulsed with the irrelevant melanoma associated peptide Melan-A/Mart-1.

Figure 7:
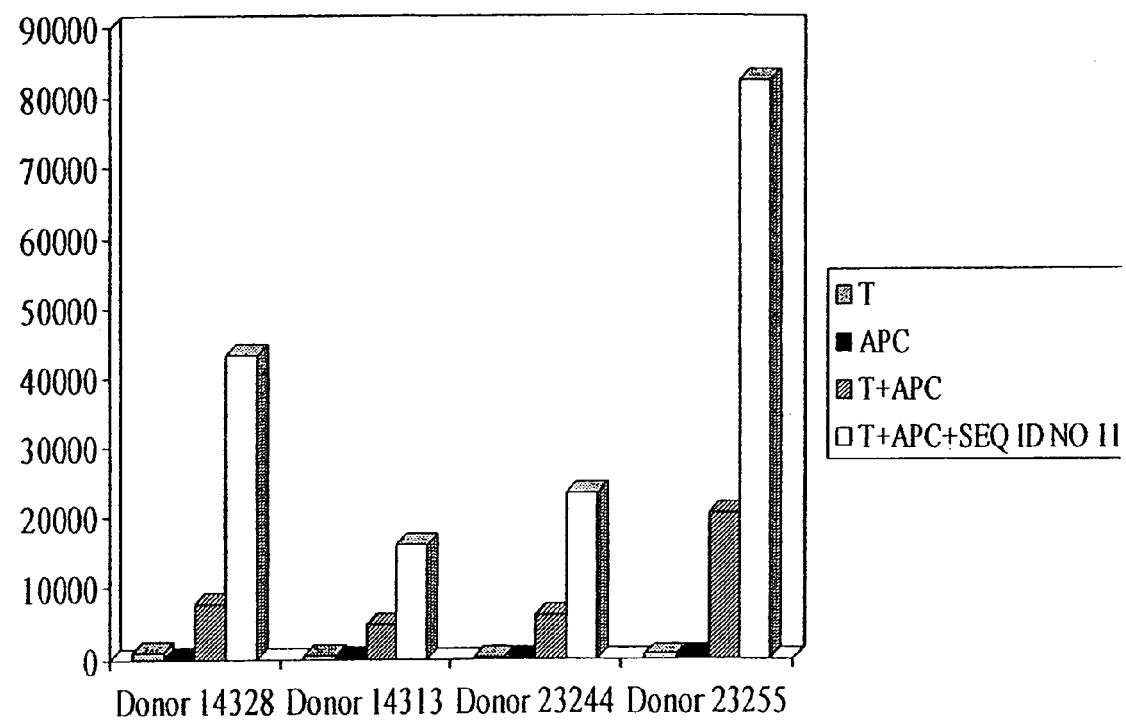
FIG. 7 shows proliferative T cell responses induced in human blood samples by a polypeptide having the amino acid sequence of SEQ ID NO: 11.

Induction and Proliferation of Human T Cell Response to the hTERT σ-Insert Peptide In this experiment, peripheral blood mononuclear cells (PBMC) from four healthy humans (donors "14328", "14313", "23244" and "23255") and were isolated and primed for seven days with dendritic cells pulsed with the SEQ ID NO: 11 peptide derived from the hTERT -insert polypeptide, followed by two cycles consisting of seven days re-stimulation with peptide-pulsed autologous PBMC. The dendritic cells were derived from monocytes from peripheral blood. T cells from the resulting bulk culture were tested in triplicate with or without peptide-pulsed antigen presenting cells (APC) before harvesting after 3 days. To measure the proliferative capacity of the cultures, $^3$H-thymidine ($3.7 \times 10^4$ Bq/well) was added to the culture overnight before harvesting. Cultures with non-pulsed APC or without APC served as controls. The results showing the proliferative capacity of the cultures are shown in FIG. 7. Further details of the protocol used are set out below.

T cell clones were obtained from the resulting bulk cultures from non-vaccinated donors 14313 and 23255. The clones were obtained from T cell blasts preset in PRMCs as described in the above section "In vitro T cell response analysis". The results of proliferation of the T cell clones with peptide-pulsed and non-peptide pulsed anitgen presenting cells are shown in FIG. 8 (donor 14313) and FIG. 9 (donor 23255).

Figure 8:
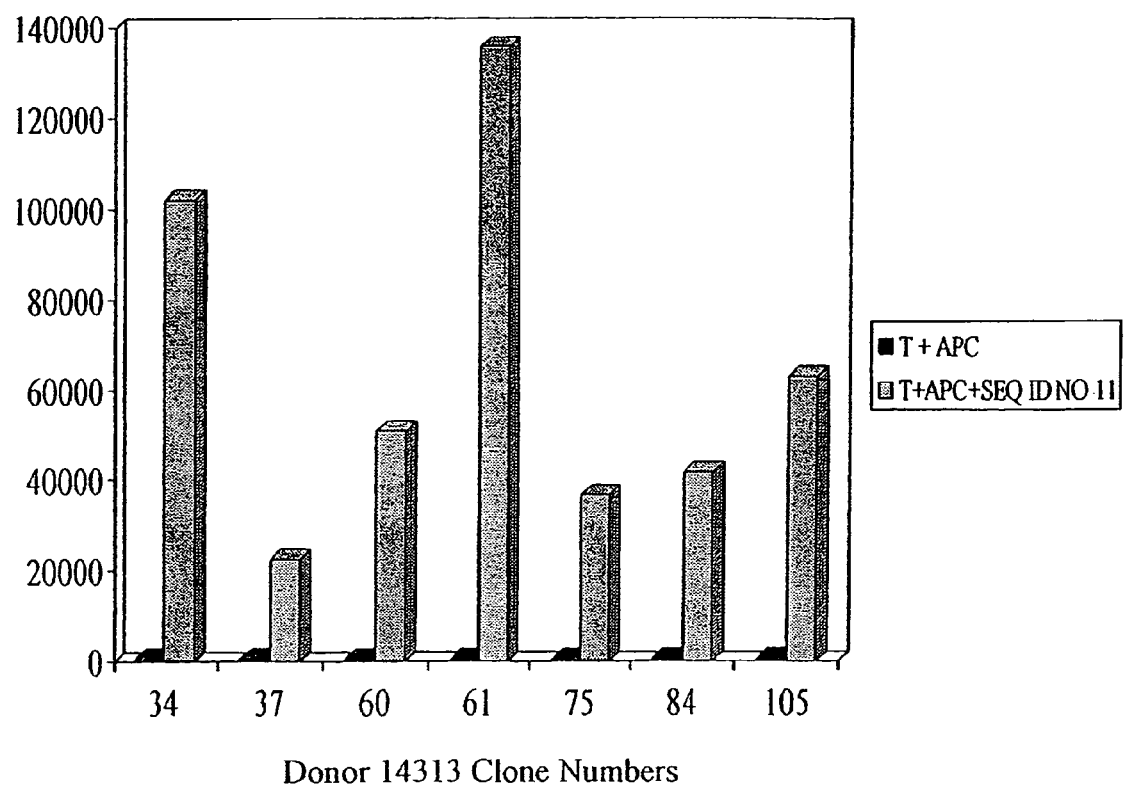
FIG. 8 shows proliferation of T cell clones induced by a polypeptide having the amino acid sequence of SEQ ID NO: 11.
Figure 9:
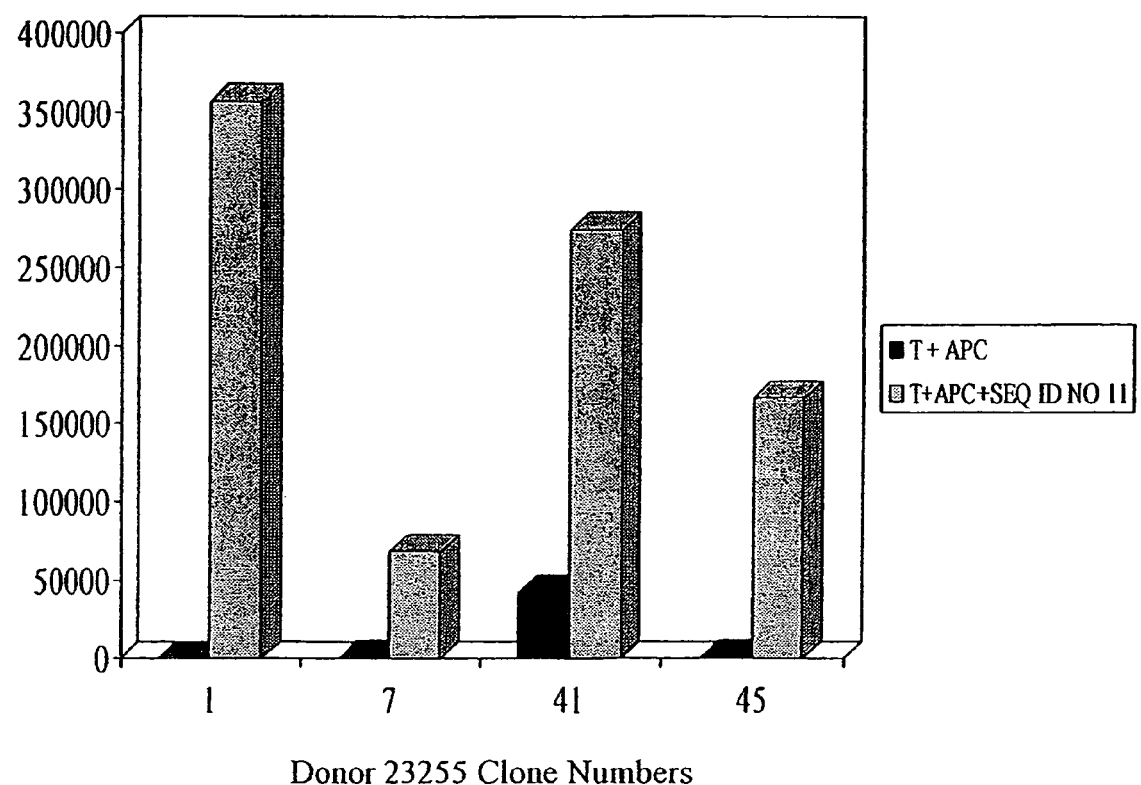
FIG. 9 shows proliferation of other T cell clones induced by a polypeptide having the amino acid sequence of SEQ ID NO: 11.

Results in FIGS. 7, 8 and 9 are given as mean counts per minute (cpm) of triplicate measurements. The data demonstrates that blood from humans contain circulating T cells specific for a peptide (SEQ ID NO: 11) derived from the peptide derived from the hTERT -insert polypeptide, and furthermore that such T cells can be expanded in vitro following stimulation with the relevant peptide.

Thus, the experiments of FIGS. 7, 8 and 9 show that the hTERT -insert polypeptide is immunogenic in man. In vitro (or in vivo) stimulation can this give rise to hTERT -insert protein-specific T cell responses with the potential to recognise the same antigen when overexpressed by a tumour growing in a cancer patient. This particular experiment demonstrates that in principle the peptide of SEQ ID NO: 11 could be developed as a cancer vaccine in humans.

Protocol for Induction of MHC Class II Restricted T Cell Response

Day 0:

PBMCs were separated out from 50 ml of blood (from buffy coat). The cells were counted and re-suspended in complete RPMI-1640/15% pool serum.

Bulk cultures were set up with 1-2 wells on a 24-well plate of PBMCs at $2 \times 10^6$ cells/ml in 1-1.5 ml. 25 µM of SEQ ID NO:11 peptide derived from the hTERT δ-insert polypeptide were added.

Day 9-10:

Bulk cultures were harvested and stimulated with irradiated PBMCs and peptide. If there was high cell death, cultures were lymphoprep separated, otherwise they were counted and resuspended in RPMI/15% pool serum. (Lymphoprep centrifugation of bulk cultures is carried out in 15 ml Falcon tubes by 1; adding 8 ml of cell suspension, and 2; underlay with 2 ml of lymphoprep. Spin at 1500 rpm for 30 min, and wash twice with salt water.) One vial of autologous PBMCs was defrosted, washed, counted and resuspended in RPMI/15% FCS. The PBMCs were irradiated (25 GY, 5 min 58 sec). Cells were plated out in 24-well plates. $0.5-2.0 \times 10^6$ T cells from bulk cultures were stimulated with $1 \times 10^6$ irradiated feeder cells (PBMCs) and 25 µM SEQ ID NO:11 peptide. The final volume was 1 ml.

Day 12:

IL-2 (10 U/ml) was added. Medium was also added if necessary by replacing half the volume. Cultures were split if necessary.

Day 17:

The T cells in bulk culture were re-stimulated as on day 10, with autologous, irradiated PBMC's and SEQ ID NO: 11 peptide.

Day 19:

IL-2 (10 U/ml) was added to day 17 re-stimulated bulk cultures.

Day 24:

A proliferation assay for testing T cells for peptide specificity was set up in 96-well plates, each condition in triplicate:

| Triplicates | 1-3 | 4-6 | 7-9 | 10-12 |
|---|---|---|---|---|
| Controls | PBMC$^1$ | Tc$^2$ | PBMC$^1$ + Tc$^2$ | PBMC$^1$ + Tc$^2$ + IL-2$^3$ |
| Test samples | PBMC$^1$ + Tc$^2$ + Pep$^4$ | PBMC$^1$ + Tc$^2$ + Pep$^4$ + IL-2$^3$ | | |

$^1$50 000 irradiated PBMCs,
$^2$50 000 T cells from bulk culture,
$^3$1 U/ml,
$^4$25 µg/ml
SEQ ID NO: 11 peptide On day 2-3 of proliferation assay, $^3$H-Thymidine (20 µl) was added, and incubated at 37 C overnight before harvesting.

In a variant of the protocol (as used in the above example) the PBMCs were, on Day 0, primed with dendritic cells pulsed with SEQ ID NO: 11.

The invention claimed is:

1. A method of stimulating an immune response in a mammal comprising the step of administering to the mammal a polypeptide that comprises a sequence of at least eight contiguous amino acids of SEQ ID NO: 5 or all of SEQ ID NO: 6 or all of SEQ ID NO: 4 or all of SEQ ID NO: 11.

2. The method of claim 1, wherein the polypeptide comprises all of SEQ ID NO: 5.

3. The method of claim 1, wherein the polypeptide comprises all of SEQ ID NO: 6.

4. The method of claim 3, wherein the polypeptide comprises all of SEQ ID NO: 11.

5. The method of claim 4, wherein the polypeptide comprises all of SEQ ID NO: 4.

6. The method of claim 2, wherein the polypeptide is up to 25 amino acids long.

7. A method of claim 3, wherein the polypeptide is up to 25 amino acids long.

8. The method of claim 4, wherein the polypeptide is up to 25 amino acids long.

9. The method of claim 1, wherein the polypeptide consists of SEQ ID NO: 5.

10. The method of claim 1, wherein the polypeptide consists of SEQ ID NO: 11.

11. The method of claim 1, wherein the polypeptide consists of SEQ ID NO. 4.

12. The method of any of claims 1-11, wherein the adjuvant GM-CSF also is administered to the human.

13. The method of any of claims 1-11, wherein there also is administered to the human one or more adjuvants selected from the group consisting of cytokines and growth factors.

* * * * *

UNITED STATES PATENT AND TRADEMARK OFFICE
CERTIFICATE OF CORRECTION

| | |
|---|---|
| PATENT NO. | : 7,375,117 B2 |
| APPLICATION NO. | : 11/391497 |
| DATED | : May 20, 2008 |
| INVENTOR(S) | : Gustav Gaudernack et al. |

It is certified that error appears in the above-identified patent and that said Letters Patent is hereby corrected as shown below:

ON THE TITLE PAGE [75]:

Inventors, "Stein Sæøe-Larssen, Oslo (NO);" should read --Stein Sæbøe-Larssen, Oslo (NO);--.

COLUMN 3:

Line 10, "hTGF -RII" should read --hTGFβ-RII--;
Line 61, "named -del (or DEL1) and -del" should read
   --named α-del (or DEL1) and β-del--;
Line 62, "The -del" should read --The α-del--; and
Line 65, "the -del" should read --the β-del--.

COLUMN 4:

Line 6, "The -insert" should read --The σ-insert--;
Line 7, "The -insert" should read --The σ-insert--;
Line 10, "The -insert" should read --The γ-insert--;
Line 23, "Others" should read --Other--;
Line 25, "Kinase C," should read --Kinase Cα,--;
Line 38, "the and splice" should read --the α and β splice--;
Line 43, "TERT and splice" should read --TERT γ and σ splice--; and
Line 57, "that that" should read --that--.

COLUMN 5:

Line 1, "domain" should read --domains--; and
Line 40, "default;" should read --default.--.

COLUMN 6:

Line 44, "(eg." should read --(e.g.,--.

UNITED STATES PATENT AND TRADEMARK OFFICE
CERTIFICATE OF CORRECTION

PATENT NO. : 7,375,117 B2
APPLICATION NO. : 11/391497
DATED : May 20, 2008
INVENTOR(S) : Gustav Gaudernack et al.

It is certified that error appears in the above-identified patent and that said Letters Patent is hereby corrected as shown below:

COLUMN 7:

Line 31, "hTERT -insert" should read --hTERT γ-insert--; and
Line 32, "hTERT -insert" should read --hTERT σ-insert--.

COLUMN 8:

Line 2, "(eg." should read --(e.g.,--;
Line 4, "(eg." should read --(e.g.,--;
Line 35, "(eg." should read --(e.g.,--;
Line 38, "hTGF -RII" should read --hTGRβ-RII--; and
Line 50, "present" should read --present invention--.

COLUMN 9:

Line 33, "(1 g)" should read --(1 μg)--;
Line 35, "1 microgram (1 g)" should read --1 microgram (1 μg)--; and
Line 38, "ie." should read --i.e.,--.

COLUMN 10:

Line 6, "hTERT -insert protein and/or the hTERT -insert" should
   read --hTERT γ-insert protein and/or the hTERT σ-insert--;
Line 18, "hTERT -insert" should read --hTERT γ-insert--;
Line 21, "hTERT -insert" should read --hTERT γ-insert--;
Line 23, "in" should read --is--;
Line 26, "hTERT -insert" should read --hTERT γ-insert--;
Line 33, "hTERT -insert" should read --hTERT γ-insert--;
Line 34, "hTERT -insert" should read --hTERT σ-insert--;
Line 37, "-insert protein and the hTERT -insert" should read
   --γ-insert protein and the hTERT σ-insert--;
Line 45, "hTERT -insert" should read --hTERT γ-insert--;
Line 49, "the -insert" should read --the σ-insert--;
Line 50, "the -insert" should read --the γ-insert--; and
Line 67, "hTERT -insert" should read --hTERT γ-insert--.

UNITED STATES PATENT AND TRADEMARK OFFICE
CERTIFICATE OF CORRECTION

PATENT NO. : 7,375,117 B2
APPLICATION NO. : 11/391497
DATED : May 20, 2008
INVENTOR(S) : Gustav Gaudernack et al.

It is certified that error appears in the above-identified patent and that said Letters Patent is hereby corrected as shown below:

COLUMN 11:

Line 1, "-insert" should read --σ-insert--;
Line 8, "hTERT -insert" should read --hTERT γ-insert--;
Line 9, "-insert" should read --σ-insert--;
Line 26, "(eg." should read --(e.g.,--;
Line 34, "(eg." should read --(e.g.,--;
Line 66, "hTERT -insert" should read --hTERT γ-insert--; and
Line 67, "-insert" should read --σ-insert--.

COLUMN 12:

Line 2, "-insert" should read --γ-insert--;
Line 5, "-insert and -insert" should read --γ-insert and σ-insert--;
Line 8, "-insert (A)" should read --γ-insert (A)--;
Line 31, "hTERT -insert" should read --hTERT γ-insert--;
Line 34, "hTERT -insert" should read --hTERT γ-insert--;
Line 36, "hTERT -insert" should read --hTERT σ-insert--;
Line 39, "hTERT -insert" should read --hTERT σ-insert--;
Line 42, "hTERT -insert" should read --hTERT γ-insert--;
Line 55, "-insert" should read --γ-insert--;
Line 57, "-insert" should read --σ-insert--;
Line 58, "-insert" should read --γ-insert--;
Line 65, "hTERT -insert and -insert" should read
   --hTERT γ-insert and σ-insert--; and
Line 67, "nomial" should read --normal--.

COLUMN 13:

Line 4, "Both and inserts" should read --Both γ and σ inserts--;
Line 8, "a -insert" should read --a γ-insert--;
Line 10, "A -insert" should read --A σ-insert--;
Line 17, "hTERT -insert and/or -insert" should read
   --hTERT γ-insert and/or σ-insert--;
Line 24, "It" should read --In--;
Line 39, "the -Insert" should read --the γ-Insert--;
Line 60, "-insert" should read --γ-insert--; and
Line 65, "-insert" should read --γ-insert--.

UNITED STATES PATENT AND TRADEMARK OFFICE
CERTIFICATE OF CORRECTION

PATENT NO. : 7,375,117 B2
APPLICATION NO. : 11/391497
DATED : May 20, 2008
INVENTOR(S) : Gustav Gaudernack et al.

It is certified that error appears in the above-identified patent and that said Letters Patent is hereby corrected as shown below:

COLUMN 14:

Line 32, "t" should read --to--; and
Line 52, "letters "I"" should read --letters "T"--.

COLUMN 15:

Line 22, "hTERT -insert" should read --hTERT γ-insert--;
Line 23, "-insert" should read --σ-insert--;
Line 35, "-insert protein and/or the hTERT -insert" should read
    --γ-insert protein and/or the hTERT σ-insert--;
Line 37, "hTERT -insert protein and/or hTERT -insert" should read
    --hTERT γ-insert protein and/or hTERT σ-insert--;
Line 38, "hTERT -insert" should read --hTERT γ-insert--;
Line 39, "hTERT -insert" should read --hTERT σ-insert--;
Line 43, "hTERT -insert" should read --hTERT γ-insert--;
Line 44, "hTERT -insert" should read --hTERT σ-insert--;
Line 46, "hTERT -insert and/or hTERT -insert" should read
    --hTERT γ-insert and/or hTERT σ-insert--;
Line 50, "-insert and/or hTERT -insert" should read
    --γ-insert and hTERT σ-insert--;
Line 57, "hTERT -insert" should read --hTERT γ-insert--; and
Line 58, "-insert" should read --σ-insert--.

COLUMN 16:

Line 8, "-insert and/or the hTERT -insert" should read
    --γ-insert and/or the hTERT σ-insert--;
Line 12, "hTERT -insert protein or hTERT -insert protein," should read
    --hTERT γ-insert protein or hTERT σ-insert protein,--;
Line 14, "hTERT -insert or hTERT -insert" should read
    --hTERT γ-insert or hTERT σ-insert--;
Line 15, "hTERT -insert and/or hTERT -insert" should read
    --hTERT γ-insert and/or hTERT σ-insert--;
Line 30, "hTERT -insert and/or hTERT -insert" should read
    --hTERT γ-insert and/or hTERT σ-insert--;
Line 33, "hTERT -insert" should read --hTERT γ-insert--;
Line 34, "hTERT -insert" should read --hTERT σ-insert--;

UNITED STATES PATENT AND TRADEMARK OFFICE
CERTIFICATE OF CORRECTION

PATENT NO. : 7,375,117 B2
APPLICATION NO. : 11/391497
DATED : May 20, 2008
INVENTOR(S) : Gustav Gaudernack et al.

It is certified that error appears in the above-identified patent and that said Letters Patent is hereby corrected as shown below:

Line 49, "37°C. before" should read --37°C before--;
Line 52, "hTERT -insert and/or hTERT -insert" should read
  --hTERT γ-insert and/or hTERT σ-insert--;
Line 57, "1 mM" should read --1 µM--;
Line 58, "mg/mL" should read --µM/mL-- and
  "37°C. before" should read --37°C before--; and
Line 59, "T cells Assays" should read --T cells. Assays--.

COLUMN 17:

Line 6, "1 mM" should read --1 µM--;
Line 7, "mg/mL" should read --µM/mL--;
Line 17, "experiment Polypeptide" should read --experiment. Polypeptide--;
Line 31, "hTERT -insert" should read --hTERT σ-insert--;
Line 46, "PRMCs" should read --PBMCs--;
Line 49, "non-peptide pulsed" should read --non-peptide-pulsed--;
Line 56, "hTERT -insert" should read --hTERT σ-insert--;
Line 61, "hTERT -insert" should read --hTERT σ-insert--; and
Line 62, "hTERT -insert" should read --hTERT σ-insert--.

COLUMN 18:

Line 10, "hTERT δ-insert" should read --hTERT σ-insert--.

Signed and Sealed this

Eighth Day of September, 2009

David J. Kappos
*Director of the United States Patent and Trademark Office*